(12) United States Patent
Kawano et al.

(10) Patent No.: US 9,107,339 B2
(45) Date of Patent: Aug. 18, 2015

(54) SEED-COVERING AGENT AND SEED COVERED WITH SEED-COVERING AGENT

(75) Inventors: Takashi Kawano, Chiba (JP); Masashi Fujinaga, Chiba (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days.

(21) Appl. No.: 13/884,032

(22) PCT Filed: Nov. 10, 2011

(86) PCT No.: PCT/JP2011/076468
§ 371 (c)(1),
(2), (4) Date: May 8, 2013

(87) PCT Pub. No.: WO2012/063970
PCT Pub. Date: May 18, 2012

(65) Prior Publication Data
US 2013/0219787 A1    Aug. 29, 2013

(30) Foreign Application Priority Data

Nov. 12, 2010  (JP) .................................. 2010-253691
Aug. 11, 2011  (JP) .................................. 2011-175768

(51) Int. Cl.
*A01C 1/06*  (2006.01)
*A01H 4/00*  (2006.01)

(52) U.S. Cl.
CPC . *A01C 1/06* (2013.01); *A01H 4/006* (2013.01)

(58) Field of Classification Search
CPC .................................. A01C 1/06; A01H 4/006

USPC ............................................ 47/57.6; 504/100
See application file for complete search history.

(56) References Cited

U.S. PATENT DOCUMENTS

2012/0190543 A1 *  7/2012  Lambert et al. ............... 504/100

FOREIGN PATENT DOCUMENTS

JP           01034203 A  *  2/1989
JP         2005192458 A  *  7/2005

OTHER PUBLICATIONS

JP 2005-192458 machine translation.*
Aug. 5, 2014 Office Action issued in U.S. Appl. No. 13/819,868.
Yamauchi, "Tetsu Kouingu Tansui Jikamaki Manyuaru 2010," National Agriculture and Food Research Organization, National Agricultural Research Center for Western Region, Mar. 2010, pp. 1-28 (with partial translation).

* cited by examiner

*Primary Examiner* — Son T Nguyen
(74) *Attorney, Agent, or Firm* — Oliff PLC

(57) ABSTRACT

A seed-covering agent, which covers a seed surface and contains an iron powder and a binder, is specified such that, in the above-described iron powder, the mass ratio of an iron powder having a particle size of 63 μm or less to a total mass of the iron powder is 0% or more and 75% or less, the mass ratio of an iron powder having a particle size of more than 63 μm and 150 μm or less to the total mass of the iron powder is 25% or more and 100% or less, and the mass ratio of an iron powder having a particle size of more than 150 μm to a total mass of the iron powder is 0% or more and 50% or less, and the average particle size of the above-described binder is 1 to 150 μm.

10 Claims, 1 Drawing Sheet

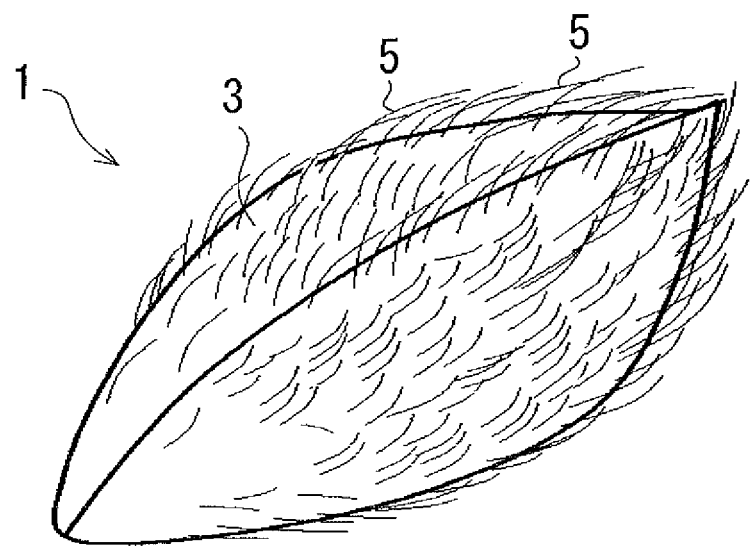

SEED-COVERING AGENT AND SEED COVERED WITH SEED-COVERING AGENT

TECHNICAL FIELD

The present invention relates to a seed-covering agent which contains an iron powder and a binder as constituents and which can cover a seed effectively. The present invention also relates to a seed covered with a seed-covering agent, wherein the seed is covered with the seed-covering agent.

BACKGROUND ART

Along with the aging of farmers and globalization of farm produce distribution, the labor savings in farm working and a production cost reduction of farm produce have been issues to be solved. In order to solve these issues, for example, in direct planting rice cultivation, a direct seeding method in which seeds are seeded directly into a farm field has become widespread for the purpose of labor savings in rearing of seeding and transplantation. Among them, a technique in which seeds covered with an iron powder are used in order to increase the specific gravity of the seeds has been noted because floating and outflow of seeds in a paddy field are prevented and, in addition, there is a merit that damage by birds is prevented.

In addition, it has also been noted that a bactericidal effect is secondarily obtained by the iron powder cover.

In order to utilize a direct seeding cultivation method by using seeds covered with an iron powder, as described above, it is required that the applied iron powder film is not peeled easily in transportation and seeding steps. This is because if the iron powder film is peeled, the specific gravity of the seed is reduced and the above-described merits are not obtained and, in addition, a peeled film causes plugging in piping and becoming entangled with a rotation mechanism portion in the transportation and seeding steps and a peeled fine iron powder also causes generation of dust. Consequently, it is necessary that peeling of the iron powder film be minimized.

As for a technology to allow an iron powder to adhere to a rice seed surface and solidify, Patent Literature 1 proposes the following technology as a method for manufacturing an iron powder-covered rice seed.

"A method for manufacturing an iron powder-covered rice seed, characterized by comprising the steps of adding an iron powder and 0.5% to 2% of sulfate (where calcium sulfate is excluded) and/or chloride on a mass ratio relative to the iron powder basis to rice seeds, performing granulation after further addition of water, allowing the iron powder to adhere to the rice seed with rust produced by supplying water and oxygen and inducing an oxidation reaction of a metal iron powder and solidify and, thereafter, performing drying." (refer to Claim 1 in Patent Literature 1)

In the invention described in Patent Literature 1, rice seeds are seeded using a power spreader or a seeding machine, so that strength characteristics at the level of not being flaked by a mechanical impact is required. Therefore, it is ascertained that the coating has practical strength on the basis of a measurement by a method for measuring a level of flaking of the coating (hereafter referred to as a coating flaking test), i.e. a method in which a mechanical impact is given by dropping the resulting coated rice seed five times from a height of 1.3 into a steel sheet having a thickness of 3 mm.

Meanwhile, according to Patent Literature 1, in the case where iron powders having particle size distributions shown in Table 1 described below are used for coatings, all of samples can maintain practical impact strength in the above-described flaking test of iron powder-covered rice seed, although the iron powder particle size distribution is not specifically noted.

TABLE 1

| | Particle size distribution (percent by mass) | | | | | |
|---|---|---|---|---|---|---|
| Type of iron powder | 45 µm or less | more than 45 µm and 63 µm or less | more than 63 µm and 75 µm or less | more than 75 µm and 106 µm or less | more than 106 µm and 150 µm or less | more than 150 µm and 180 µm or less |
| DSP317 | 85 | 15 | 0 | 0 | 0 | 0 |
| 270M-200 | 34.1 | 43.2 | 14.6 | 6.1 | 1.1 | 0.9 |
| DNC-300 | 85 | 10 | 5 | 0 | 0 | 0 |
| Atomized | | | 180 µm or less (unspecified) | | | |

CITATION LIST

Patent Literature

PTL 1: Japanese Patent No. 4441645

Non Patent Literature

NPL 1: "Observation of Microscopic Structure of Rice" (by Takamasa Mesaki, Japanese Society of Taste Technology, 2006, p. 20-21)

NPL 2: "Manual of Direct Seeding of Iron Coating in Flooded Field 2010" (by Minoru Yamauchi, edited by The National Agriculture and Food Research Organization Western Region Agricultural Research Center, March 2010)

NPL 3: JPMA P 11-1992 "Method for Measuring Rattler Value of Metal Green Compact" (Japan Powder Metallurgy Association Standard, 1992)

SUMMARY OF INVENTION

Technical Problem

However, the present inventors found new problems in the related art, as described below.

As for the adhesion strength of an iron powder film, in Patent Literature 1, flaking of the iron powder cover due to an impact resulting from dropping in especially a seeding step is studied. Therefore, the flaking test, in which a mechanical impact is given by dropping five times from a height of 1.3 m to a steel sheet having a thickness of 3 mm, is performed as a strength test.

However, as described above, the rice seed is applied with a mechanical external force in not only the seeding step, but also the transportation step. In this regard, the mechanical external forces applied to the rice seed in the transportation step are an impact due to dropping and, in addition, frictional forces, e.g., slipping and rolling, generated between seeds or between seeds and a container.

In the case where an iron powder cover undergoes an impact due to dropping, the iron powder cover is peeled by cracking. However, in the case where the iron powder cover undergoes a frictional force, a form of gradual peeling due to wearing down is exhibited.

Consequently, as for the iron powder cover, in order to prevent peeling of the iron powder film in not only the seeding step, but also the transportation step, a cover having strength against the frictional force is necessary.

However, there has been no technology which realizes an iron powder capable of covering rice seeds with sufficient strength against frictional stresses of slipping and rolling of seeds and seeds covered with an iron powder.

Meanwhile, as shown in Table 1, in the particle size distribution of the iron powder described in Patent Literature 1, the proportion of the particle size of 63 μm or less is large.

However, in the case where a fine iron powder is used, the iron powder reacts with oxygen in the air rapidly, and a seed covered with the iron powder may be damaged by generated heat. Furthermore, in the case where a large amount is handled, a fire prevention measure is required. In addition, a fine iron powder generates dust easily and, therefore, there is a problem in that a clean operation environment is not maintained easily.

Meanwhile, Patent Literature 1 discloses that a binder is added in order to strengthen adhesion of the iron powder to the rice seed and that a sulfate and/or a chloride is added as a binder, water is further added, and granulation is performed. Then, in the specific granulation method, the iron powder, the sulfate and/or the chloride, and the rice seeds are put into a rotary container, and rice seed surfaces are coated with the iron powder and gypsum while water is sprayed.

However, if the above-described granulation method is used in Patent Literature 1, agglomerated particles of the iron powder and the binder are generated easily.

The agglomerated particles cause various problems in that reduction in the yield of adhesion of the iron powder to the rice seeds is induced, the homogeneity of the film components is impaired, and furthermore, operability of covering is degraded and, therefore, is very harmful.

The present invention has been made to solve the above-described problems and it is an object to obtain a seed-covering agent which can realize a cover with reduced falling of the iron powder in not only a seeding step, but also a transportation step, and a seed covered with the seed-covering agent.

Also, it is an object to obtain a seed-covering agent which has low possibility to damage a rice seed and which is easy-to-handle and a seed covered with the seed-covering agent.

Solution to Problem

In order to solve the above-described problems, the inventors performed studies on each of an iron powder and a binder, as described below.

<Study on Iron Powder>

The inventors observed the surface of a rice seed and, thereby, studied what type of iron powder was used for preventing peeling effectively.

The inventors noted the surface state of the rice seed. As shown in FIG. 1, hairs 5 grow on a surface of a rice hull 3 which is an outermost hull of a seed rice 1. It is estimated that, in coating of the seed rice 1 with an iron powder, the adhesion is enhanced through holding of the iron powder by the hairs 5, where the iron powder is disposed between a hair 5 and a hair 5 by an elastic action of the hairs 5.

There are variations in density in the manner of growing of the above-described hairs 5, as described in page 21 of "Observation of Microscopic Structure of Rice (by Takamasa Mosaki)" (Non Patent Literature 1) as well. In particular, it is believed that the adhesion is enhanced by the iron powder being held by the hairs 5 in a portion crowded with hairs 5. The interval of hairs 5 in this portion is 50 to 150 μm.

Consequently, the inventors considered that there was an appropriate range of particle size of the iron powder which can firmly adhere to the rice seed because of the holding action by the hairs 5 and performed study on the iron powder particle size to exert this holding action effectively. As a result, it was found that the particle size was preferably more than 63 μm and 150 μm or less.

Therefore, it was found that holding by the hairs 5 was able to be expected and the amount of peeling of the cover film was able to be reduced when particles having a particle size of more than 63 μm and 150 μm or less were contained to some extent.

In addition, the inventors performed study on the particle size of an iron powder which slips through the hairs 5 and adheres directly to the rice seed surface, besides adhesion by holding force of the hairs 5 of the rice seed.

In general, a powder having a smaller particle size has higher adhesion to the subject of adhesion. Therefore, it is preferable that the particle size of the iron powder be smaller from the viewpoint of direct adhesion to the rice seed surface.

As a result of study on the particle size of an iron powder which was expected to slip through the hairs 5 of the rice seed and adhere directly to the rice seed surface, it was found that containment of a predetermined amount of iron powder of 45 μm or less was preferable.

Then, it was found that in the case where the above-described iron powder having a fine particle size was contained in addition to the iron powder held by the hairs 5, the iron powder having a fine particle size adhered to the surface of the rice seed, the iron powder was held by the hairs 5 above the iron powder having a fine particle size and, thereby, the amount of peeling of the cover film along with slipping and rolling was able to be reduced because double coating with the iron powder was provided.

In this regard, it is necessary that the amount be less than or equal to a predetermined amount because if a large amount of iron powder having a fine particle size is contained, the above-described problems occur.

Meanwhile, it is estimated that if the particle size of the iron powder is too large, the iron powder particle becomes difficult to enter into a gap between hairs 5 and, in addition, an adhesion effect is reduced because the gravity applied to the iron powder particle is large and the hairs 5 becomes difficult to hold the iron powder particle. Consequently, it was also found that the proportion of iron powder having a particle size of 150 μm or more was specified to be preferably less than or equal to a predetermined amount.

<Study on Binder>

As for the binder, a cause of generation of agglomerated particles was studied. As a result, it was found that generation of agglomerated particles related to the particle size of the binder.

In this regard, the above-described study has been explained with reference to the rice seed as an example, although the effects of the present invention are expected with respect to even other seeds in the case where the seed has hairs on the surface as with the rice seed, and the manner of growth of hairs (interval and the like) is analogous to that of the rice seed. Examples of seeds having hairs on the surface include seeds of wheat, carrot, and tomato.

The present invention has been made on the basis of the above-described findings and, specifically, includes the following configurations.

(1) A seed-covering agent according to the present invention is a seed-covering agent which is used for covering a seed surface and which contains an iron powder and a binder, wherein, in the above-described iron powder, the mass ratio of an iron powder having a particle size of 63 μm or less to a total mass of the iron powder is 0% or more and 75% or less, the mass ratio of an iron powder having a particle size of more than 63 μm and 150 μm or less to the total mass of the iron powder is 25% or more and 100% or less, and the mass ratio of an iron powder having a particle size of more than 150 μm to the total mass of the iron powder is 0% or more and 50% or less, and the average particle size of the above-described binder is 1 to 150 μm.

The iron powder and the binder may be present as a mixture mixed before an operation to cover the seed or be present independently before the seed is covered and be mixed together with the seed in covering.

(2) In this regard, in the agent according to the above-described item (1), the above-described binder contains at least one type selected from sulfates and chlorides.

(3) Also, in the agent according to the above-described item (1) or item (2), the mass ratio of an iron powder having a particle size of more than 63 μm and 150 μm or less is 50% or more in the above-described iron powder.

(4) Also, in the agent according to any one of the above-described items (1) to (3), the mass ratio of an iron powder having a particle size of 45 μm or less to the total mass of the iron powder is 0% or more and 30% or less in the above-described iron powder.

(5) Also, in the agent according to any one of the above-described items (1) to (4), the above-described iron powder is an iron powder produced by a reduction process or an atomizing process.

(6) A seed covered with a seed-covering agent, according to the present invention, is produced by covering the seed with the seed-covering agent according to any one of the above-described items (1) to (5).

(7) Also, in the seed according to the above-described item (6), the above-described seed is a rice seed.

In this regard, the seed covered with a seed-covering agent, according to the present invention, preferably has a cover layer which is held by hairs included in the seed and which contains the iron powder and the binder, and the average particle size of the iron powder contained in the cover layer is preferably 63 to 150 μm.

Further preferably, the seed covered with a seed-covering agent, according to the present invention, has a first cover layer, which contains an iron powder and a binder, on the surface in close proximity to the seed, and has a second cover layer, which is held by hairs included in the seed and which contains an iron powder and a binder, above the first cover layer. Here, the iron powder contained in the first cover layer is preferably fine particles, and further preferably the particle size is 45 μm or less. Further preferably, the average particle size of the iron powder contained in the first cover layer is 1 to 40 μm. Meanwhile, the iron powder contained in the second cover layer is preferably relatively coarse, and further preferably the particle size is 63 to 150 μm.

Advantageous Effects of Invention

The seed-covering agent according to the present invention has the following effects because, in the iron powder, the mass ratio of an iron powder having a particle size of 63 μm or less to a total mass of the iron powder is 0% or more and 75% or less, the mass ratio of an iron powder having a particle size of more than 63 μm and 150 μm or less to the total mass of the iron powder is 25% or more and 100% or less, and the mass ratio of an iron powder having a particle size of more than 150 μm to the total mass of the iron powder is 0% or more and 50% or less, and the average particle size of the binder is 1 to 150 μm.

It can be expected that the iron powder be held by hairs of a seed, e.g., a rice seed, having hairs on the seed surface, and a cover with reduced falling of the iron powder in not only a seeding step, but also a transportation step can be realized.

The binder can suppress generation of agglomerated particles and, therefore, an improvement in yield, homogenization of cover components and, in addition, an improvement in operability of covering can be realized.

According to them, the labor savings in farm working and a production cost reduction of farm produce become possible.

BRIEF DESCRIPTION OF DRAWINGS

FIG. 1 is an explanatory diagram illustrating the surface state of a rice seed.

DESCRIPTION OF EMBODIMENTS

A seed-covering agent according to an embodiment of the present invention is a seed-covering agent which is used for covering a seed surface and which contains an iron powder and a sulfate and/or a chloride serving as a binder and is characterized in that, in the above-described iron powder, the mass ratio of an iron powder having a particle size of 63 μm or less to a total mass of the iron powder is 0% or more and 75% or less, the mass ratio of an iron powder having a particle size of more than 63 μm and 150 μm or less to the total mass of the iron powder is 25% or more and 100% or less, and the mass ratio of an iron powder having a particle size of more than 150 μm to the total mass of the iron powder is 0% or more and 50% or less, and the average particle size of the above-described binder is 1 to 150 μm.

The iron powder and the binder constituting the seed-covering agent will be described below in detail.

<Iron Powder>

The mass ratio of an iron powder having a particle size of more than 63 μm and 150 μm or less to the total mass of the iron powder is specified to be 25% or more for reasons described below. The iron powder having a particle size of more than 63 μm and 150 μm or less has a high possibility of being held by hairs on the seed surface. In the case where 25% or more of iron powder having such a particle size is contained, it can be expected that the iron powder be held by hairs, and a cover with reduced falling of the iron powder in not only a seeding step, but also a transportation step can be realized. The mass ratio of an iron powder having a particle size of more than 63 μm and 150 μm or less is preferably 30% or more, and more preferably 50% or more. In this regard, a substantially all amount of iron powder may be more than 63 μm and 150 μm or less and, therefore, the upper limit is specified to be 100%. A preferably upper limit is 75%.

Meanwhile, the mass ratio of an iron powder having a particle size of 63 μm or less to the total mass of the iron powder is specified to be 75% or less for reasons described below. If the content of iron powder having a fine particle size increases, the iron powder reacts with oxygen in the air rapidly, and a seed covered with the iron powder may be damaged by generated heat. Furthermore, in the case where a large amount is handled, a fire prevention measure is required. In addition, if the content of fine iron powder increases, dust is generated easily and a clean operation environment is not maintained easily. It is preferable that the mass ratio of an iron powder having a particle size of 63 μm or less be 70% or less. The iron powder having a particle size of 63 μm or less may not be contained in practice (that is, may be 0%), although it is not necessary to reduce the particle size excessively at a cost. A preferable lower limit is 25%.

In this regard, as for an aspect of more preferable content of the iron powder having a particle size of 63 μm or less, the mass ratio of an iron powder having a particle size of 45 μm or less is 0% or more and 30% or less.

The iron powder having a particle size of 45 μm or less has strong adhesion, so as to slip through hairs on seed surface and adhere directly to the seed surface and, therefore, containment of a predetermined amount (preferably 5% or more) realizes the above-described double cover. In this regard, the average particle size of the iron powder having a particle size of 45 μm or less is preferably about 1 to 40 μm.

The purport of specifying the mass ratio of an iron powder having a particle size of more than 150 μm to be 50% or less is that the iron powder having this particle size is reduced because neither holding of the iron powder having a particle size of more than 150 μm by hairs nor direct adhesion to a seed surface can be expected. The mass ratio is preferably 20% or less. The iron powder having a particle size of more than 150 μm may not be contained in practice (that is, may be 0%).

Meanwhile, the particle size distribution of the iron powder can be evaluated on the basis of screening by using a method defined in JIS Z2510-2004.

As for a method for manufacturing the iron powder in the present embodiment, any publicly known method can be applied. Specific examples include a reduction process to produce by reducing mill scale (the resulting iron powder is referred to as a reduced iron powder) and an atomizing process to produce by atomizing a molten steel with water or the like (the resulting iron powder is referred to as an atomized iron powder). The iron powder may contain alloy components and impurities besides iron, although about 10 percent by mass or less is preferable. In particular, a so-called pure iron powder containing 90 percent by mass or more of Fe is preferable.

<Binder>

The binder is formed from a sulfate and/or a chloride. Preferable sulfates are calcium sulfate, potassium sulfate, magnesium sulfate, and hydrates thereof. Also, preferable chlorides are potassium chloride, calcium chloride, magnesium chloride, and hydrates thereof.

The mass ratio of the binder contained in the whole seed-covering agent is preferably 0.1 to 80 percent by mass. This is because if the content ratio of the binder is 0.1 percent by mass or more, the strength of the film is not reduced and, therefore, is suitable for the practical use.

In addition, if the content ratio of the binder is 80 percent by mass or less, the binder is not agglomerated and the operability is not degraded. Furthermore, there is an advantage for an effect of increasing the specific gravity of the seed covered with a seed-covering agent, which is an original purpose.

In this regard, a more preferable range of the mass ratio of the binder contained in the whole seed-covering agent is 0.5 to 35 percent by mass. This is because this range is more preferable to increase the strength of the cover and prevent agglomeration of the binder.

The average particle size of the binder is specified to be 1 to 150 μm. This is because if the average particle size of the binder is less than 1 μm, agglomerated particles generated in the operation of covering increases, and the operability is degraded significantly. On the other hand, it is because if the average particle size of the binder is more than 150 μm, the adhesion of the iron powder is degraded, and the strength of the coating film is reduced. A preferable average particle size is 3 μm or more. A more preferable average particle size is 5 to 100 μm. The lower limit value may be 10 μm or more.

A method for covering a seed with the iron powder constituting the above-described seed-covering agent is not limited.

For example, as shown in "Manual of Direct Seeding of Iron Coating in Flooded Field 2010 (edited by The National Agriculture and Food Research Organization Western Region Agricultural Research Center)" (Non Patent Literature 2) p. 6-14, any one of manual covering (coating), a previously known method by using a mixer, and other methods may be used.

Examples of usable mixers include agitation impeller type mixers (for example, a Henschel mixer) and container rotation type mixers (for example, a V-type mixer, a double-cone mixer, a disk pelletizer, and a rotary hoe type mixer).

In addition, as shown in "Manual of Direct Seeding of Iron Coating in Flooded Field 2010" cited above, a binder is used in iron powder coating.

As for the specific method for covering the seed with the iron powder, the iron powder, the binder, and the seed may be put into the above-described mixer, and the mixer may be rotated while water is sprayed.

Additives other than the iron powder and the binder may be further used. However, it is preferable that a solid content serving as cover components be about 30% or less relative to the total of the iron powder and the binder.

The seed covered as described above with the seed-covering agent is the seed covered with a seed-covering agent, according to the present invention. A rice seed is a typical example of the seed to be covered, and examples of other seeds include seeds of wheat, carrot, and tomato.

EXAMPLES

Examination of Effect of Iron Powder Particle Size

In order to examine effects of the iron powder constituting the seed-covering agent according to the present invention, rice seeds were covered by using Invention examples 1 to 9, which were iron powders having various particle size distributions, as invention examples of the present invention. In addition, rice seeds were covered by using Comparative examples 1 to 5, which were iron powders having various particle size distributions out of the range of the particle size distribution according to the present invention, as comparative examples. In this regard, calcined gypsum (calcium sulfate·½ hydrates) having an average particle size of 51 μm was used as the binder.

The covering (coating) with the seed-covering agent was performed by a method in conformity with the method described in "Manual of Direct Seeding of Iron Coating in Flooded Field 2010" cited above. Specifically, the method was as described below.

Initially, a rice seed, calcined gypsum, and several types of iron powders (so-called pure iron powders) were prepared. Subsequently, a disk pelletizer was used, 10 kg of seed (rice seed) was coated with 5 kg of iron powder and 0.5 kg of calcined gypsum while an appropriate amount of water was sprayed and, furthermore, finishing was made by coating with 0.25 kg of calcined gypsum.

A method for evaluating the strength of a coating film against rolling friction and slipping friction of a seed covered (coated) with the seed-covering agent has not been established.

Then, the film strength was examined by a method in conformity with the testing method described in JPMA P 11-1992 "Method for Measuring Rattler Value of Metal Green Compact" (Non Patent Literature 3). In this regard, the present testing method is referred to as a Rattler test.

In the Rattler test, 20±0.05 g of seed coated with a seed-covering agent was sealed into a cage of a Rattler tester, and the resulting cage was rotated at a rotation speed of 87±10 rpm, where the number of revolutions was 1,000. According to this method, seeds are fluidized in the cage while being rolled and, thereby, frictional forces of rolling and slipping are loaded between seeds and between seeds and the container inside surface.

Consequently, the strength of a coating film in the case where a rolling frictional force and a slipping frictional force are loaded in combination can be evaluated by applying the present method.

Table 2 shows the particle size distribution of the iron powder and the weight reduction rate in the Rattler test. In this regard, the weight reduction rate was determined on the basis of the following calculation formula.

weight reduction rate=(mass of film peeled in Rattler test)/(seed weight before test)×100(%)

Therefore, it can be decided that as the weight reduction rate becomes small, the strength of the film becomes higher.

is 0% or more and 75% or less, the mass ratio of an iron powder having a particle size of more than 63 μm and 150 μm or less is 25% or more and 100% or less, and the mass ratio of an iron powder having a particle size of more than 150 μm is 0% or more and 50% or less", and the weight reduction rates in the Rattler test are less than 4.0%.

On the other hand, in Comparative examples 1 to 5 which are out of the above-described range of the particle size distribution, the weight reduction rates in the Rattler test are 4.0% or more.

Consequently, it was demonstrated that the weight reduction rate was able to be reduced to a great extent by specifying the particle size distribution of the iron powder to be within the range according to the present invention.

In this connection, in Table 2, numerical values of the particle size distribution of Comparative examples 1 to 5, which are out of the range according to the present invention, are underlined.

Meanwhile, in Invention examples 1, 2, 3, 4, 6, the mass ratios of iron powders having a particle size of more than 63 μm and 150 μm or less are 50% or more, and the mass ratios of iron powders having a particle size of 45 μm or less are 30% or less. The weight reduction rates of them in the Rattler test are 3.5% or less and, therefore, are low. Consequently, it is clear that the adhesion of the iron powder can be more enhanced by increasing the mass ratio of an iron powder having a particle size of more than 63 μm and 150 μm or less and reducing the mass ratio of an iron powder having a particle size of 45 μm or less.

TABLE 2

| | | Particle size distribution (percent by mass) | | | | 63 μm or less in total (percent by mass) | Weight reduction rate in Rattler test (percent by mass) |
|---|---|---|---|---|---|---|---|
| | Type of iron powder | 45 μm or less | more than 45 μm and 63 μm or less | more than 63 μm and 150 μm or less | more than 150 μm | | |
| Invention example 1 | reduced iron powder | 23.6 | 14.6 | 59.5 | 2.3 | 38.2 | 3.1 |
| Invention example 2 | reduced iron powder | 26.0 | 20.2 | 53.8 | 0.0 | 46.2 | 2.9 |
| Invention example 3 | reduced iron powder | 16.8 | 13.3 | 67.7 | 2.2 | 30.1 | 2.9 |
| Invention example 4 | reduced iron powder | 1.2 | 6.8 | 91.5 | 0.5 | 8.0 | 3.2 |
| Invention example 5 | atomized iron powder | 34.2 | 14.0 | 39.7 | 12.1 | 48.2 | 3.7 |
| Invention example 6 | atomized iron powder | 28.1 | 14.1 | 50.0 | 7.8 | 42.2 | 3.5 |
| Invention example 7 | atomized iron powder | 8.6 | 19.4 | 31.0 | 41.0 | 28.0 | 3.9 |
| Invention example 8 | reduced iron powder | 33.5 | 31.9 | 33.4 | 1.2 | 65.4 | 3.6 |
| Invention example 9 | reduced iron powder | 34.5 | 40.3 | 25.0 | 2.5 | 74.8 | 3.8 |
| Comparative example 1 | reduced iron powder | 53.2 | 45.8 | <u>1.0</u> | 0.0 | <u>99.0</u> | 4.4 |
| Comparative example 2 | reduced iron powder | 97.6 | 1.2 | <u>0.6</u> | 0.6 | <u>98.8</u> | 5.6 |
| Comparative example 3 | reduced iron powder | 37.0 | 41.6 | <u>20.5</u> | 0.8 | <u>78.6</u> | 6.8 |
| Comparative example 4 | atomized iron powder | 3.1 | 9.9 | 32.8 | <u>54.2</u> | 13.0 | 13.8 |
| Comparative example 5 | reduced iron powder | 34.7 | 42.2 | <u>22.0</u> | 1.1 | <u>76.9</u> | 4.4 |

As shown in Table 2, all of those described in Invention examples 1 to 9 exhibit the particle size distributions within the range according to the present invention, that is, "the mass ratio of an iron powder having a particle size of 63 μm or less <Examination of Effect of Binder Average Particle Size No. 1>

Next, experiments to examine effects of the average particle size of the binder were performed. As for the binder, calcined gypsum was used, and as shown in Table 3, binders having a plurality of average particle sizes were prepared. Meanwhile, as for the iron powder, the iron powder used in Invention example 1 used in the above-described experiment was employed, where in the particle size distribution, 45 μm or less was 23.6%, more than 45 μm and 60 μm or less was 14.6%, more than 63 μm and 150 μm or less was 59.5%, and more than 150 μm was 2.3%.

The method for covering the rice seed with the seed-covering agent was the same method as that employed in the above-described "Examination of effect of iron powder particle size".

The state of generation of agglomerated particles, which were generated in the operation of covering, that is, when the iron powder, the calcined gypsum, and the rice seeds were put into the disk pelletizer and were mixed, was visually checked, so as to be evaluated.

In addition, after the operation of covering was completed, the film strength of the rice seed covered with the iron powder was examined by the Rattler test.

The results are shown in Table 3.

TABLE 3

| No. | Calcined gypsum Average particle size (μm) | Agglomerated particles generated in operation | Weight reduction rate in Rattler test (%) | Conforming/ nonconforming |
|---|---|---|---|---|
| 1 | 0.6 | many | 5.8 | nonconforming |
| 2 | 12 | few | 3.7 | conforming |
| 3 | 21 | few | 3.6 | conforming |
| 4 | 51 | few | 3.2 | conforming |
| 5 | 145 | few | 3.8 | conforming |
| 6 | 203 | few | 15.2 | nonconforming |
| 7 | 1.2 | few | 3.9 | conforming |

As for the agglomerated particles, it was ascertained from the results shown in Table 3 that when the average particle size of the calcined gypsum was 0.6 μm, many agglomerated particles were generated in the operation of covering, and when the average particle size of the calcined gypsum was 1 μm or more, agglomerated particles generated in the operation of covering were few.

Meanwhile, as for the cover strength, it was ascertained that when the average particle size of the calcined gypsum was 0.6 μm, the weight reduction rate in the Rattler test was a large 5.8%, whereas when the average particle sizes of the calcined gypsum were within the range of 1.2 to 145 μm, the weight reduction rates were less than 4.0% and were within an acceptable range, and when the average particle size of the calcined gypsum was 203 μm, the weight reduction rate was a very large 15.2%.

<Examination of Effect of Binder Average Particle Size No. 2>

Next, potassium chloride was used as the binder, and experiments to examine effects of the average particle size of the binder were performed. As shown in Table 4, binders having a plurality of average particle sizes were prepared. Meanwhile, as for the iron powder, the iron powder used in Invention example 1 used in the above-described experiment was employed, where in the particle size distribution, 45 μm or less was 23.6%, more than 45 μm and 60 μm or less was 14.6%, more than 63 μm and 150 μm or less was 59.5%, and more than 150 μm was 2.3%.

The method for covering the rice seed with the seed-covering agent was the same method as that employed in the above-described "Examination of effect of iron powder particle size".

The state of generation of agglomerated particles, which were generated in the operation of covering, that is, when the iron powder, potassium chloride, and the rice seeds were put into the disk pelletizer and were mixed, was visually checked, so as to be evaluated.

In addition, after the operation of covering was completed, the film strength of the rice seed covered with the iron powder was examined by the Rattler test.

The results are shown in Table 4.

TABLE 4

| No. | Potassium chloride Average particle size (μm) | Agglomerated particles generated in operation | Weight reduction rate in Rattler test (%) | Conforming/ nonconforming |
|---|---|---|---|---|
| 1 | 0.5 | many | 4.3 | nonconforming |
| 2 | 1.5 | few | 3.5 | conforming |
| 3 | 10 | few | 3.6 | conforming |
| 4 | 140 | few | 3.7 | conforming |
| 5 | 250 | few | 10.3 | nonconforming |

It was ascertained from the results shown in Table 4 that when the average particle size of potassium chloride was 0.5 μm, many agglomerated particles were generated in the operation of covering, and when the average particle size of potassium chloride was 1 μm or more, agglomerated particles generated in the operation of covering were few.

Meanwhile, as for the cover strength, it was ascertained that when the average particle size of potassium chloride was 0.5 μm, the weight reduction rate in the Rattler test was a large 4.3%, whereas when the average particle sizes of potassium chloride were within the range of 1.5 to 140 μm, the weight reduction rates were less than 4.0% and were within an acceptable range, and when the average particle size of potassium chloride was 250 μm, the weight reduction rate was a very large 10.3%.

It was demonstrated from the above-described results that the average particle sizes of the calcined gypsum and potassium chloride serving as the binders related to generation of agglomerated particles and the cover strength.

Then, it was also ascertained that a preferable range of the average particle size of the binder was 1 to 150 μm.

Meanwhile, in the above-described examples, explanations have been made with reference to the calcined gypsum and potassium chloride as the binders. However, the same goes for other sulfates, chlorides, or mixtures of sulfates and chlorides. Furthermore, besides the sulfates and the chlorides, substances which facilitate an oxidation reaction of the iron powder, such as, sulfites, sulfides, nitrates, nitrites, hydrates of these salts, and mixtures of these salts, can be used as the binders.

In this regard, among the above-described binders, the calcined gypsum is especially favorable because of a very small adverse effect on plants and human bodies, a low price, and ease of availability.

The binder may contain about 10% or less of additives and impurities other than those described above.

INDUSTRIAL APPLICABILITY

According to the present invention, it can be expected that holding by hairs of a seed, e.g., a rice seed, having hairs on the seed surface, and a cover with reduced falling of an iron powder in not only a seeding step, but also a transportation step can be realized. Meanwhile, generation of agglomerated particles of a binder can be suppressed and, therefore, an improvement in yield, homogenization of cover components and, in addition, an improvement in operability of covering can be realized.

REFERENCE SIGNS LIST 1 seed rice
3 rice hull
5 hair

The invention claimed is:

1. A seed covered with a seed-covering agent including an iron powder component, the seed-covering agent comprising;
   a first cover layer containing fine iron particles having an average particle size from 1 μm to 40 μm in the iron powder component and a binder, and
   a second cover layer, located above the first cover layer, containing coarse iron particles having an average particle size from 63 μm 150 μm in the iron powder component and a binder; and
   wherein, in the iron powder component, (i) a mass ratio of the iron particles having a particle size of not more than 63 μm to a total mass of the iron powder component is 8% to 75% and (ii) a mass ratio of the iron particles having a particle size of more than 63 μm and not more than 150 μm to the total mass of the iron powder component is 25% to 91.5%.

2. The seed covered with the seed-covering agent according to claim 1, wherein the binder in the first cover layer and the binder in the second cover layer comprises at least one type selected from sulfates and chlorides.

3. The seed covered with the seed-covering agent according to claim 1, wherein the mass ratio of the iron particles having a particle size of more than 63 μm and not more than 150 μm is 50% to 91.5%.

4. The seed covered with the seed-covering agent according to claim 1, wherein a mass ratio of the iron particles having a particle size of not more than 45 μm to the total mass of the iron powder component is 1.2% to 30% powder component.

5. The seed covered with the seed-covering agent according to claim 4, wherein the mass ratio of the iron particles having a particle size of not more than 45 μm to the total mass of the iron powder component is 5% to 30% powder component.

6. The seed covered with the seed-covering agent according to claim 1, wherein the iron powder component is an iron powder produced by a reduction process or an atomizing process.

7. The seed covered with the seed-covering agent according to claim 1, wherein the seed is a rice seed.

8. The seed covered with the seed-covering agent according to claim 1, wherein the mass ratio of the iron particles with a particle size of not more than 63 μm to a total mass of the iron powder component is 25% to 75%.

9. The seed covered with the seed-covering agent according to claim 1, wherein the mass ratio of the iron particles having a particle size of not more than 63 μm to a total mass of the iron powder component is 28% to 75.

10. The seed covered with the seed-covering agent according to claim 1, wherein a mass ratio of the iron powder particles having a particle size of more than 150 μm is 0.5% to 50%.

* * * * *